United States Patent [19]

Musha

[11] Patent Number: 4,725,140
[45] Date of Patent: Feb. 16, 1988

[54] METHOD OF MEASURING SPECIFIC BINDING REACTION WITH THE AID OF POLARIZED LIGHT BEAM AND MAGNETIC FIELD

[75] Inventor: Toshimitsu Musha, 13-17, Minamitsukushino 2-Chome, Machida City, Tokyo, Japan

[73] Assignees: Olympus Optical Co., Ltd.; Toshimitsu Musha, both of Tokyo, Japan

[21] Appl. No.: 925,068

[22] Filed: Oct. 30, 1986

[30] Foreign Application Priority Data

Nov. 19, 1985 [JP] Japan .................. 60-256545

[51] Int. Cl.⁴ .................. G01N 15/02; G01J 4/00
[52] U.S. Cl. .................. 356/336; 356/364
[58] Field of Search ........... 356/335, 336, 338, 339, 356/364; 364/576

[56] References Cited

U.S. PATENT DOCUMENTS 4,158,234 6/1979 Grandchamp .................. 356/336
4,521,522 6/1985 Lundstrom et al. .

FOREIGN PATENT DOCUMENTS 3014036 10/1980 Fed. Rep. of Germany .

OTHER PUBLICATIONS

"Non-isotopic Immunoassay Methods", by Graham H. Beastall; Laboratory Practice, May 1985; pp. 74, 77, 78, and 81.
"Nephelometric Assay of Antigens and Antibodies with Latex Particles", by Grange Roch, and Quash; Journal of Immunological Methods, vol. 18; 1977; pp. 365–375.

Primary Examiner—Gene Wan
Attorney, Agent, or Firm—Parkhurst & Oliff

[57] ABSTRACT

A coherent light beam is made incident upon a cell via a polarizer. In the cell is contained a reaction liquid consisting of fine magnetic particles having an antibody coated thereon and a sample containing an antigen which is specifically reacted with the antibody on the particles. The particles are rotated in the reaction liquid by means of alternating magnetic fields having a frequency $f_0$ and generated by coils arranged beside the cell. Light scattered by the particles is made incident upon a photodetector via a polarizer whose polarization plane is perpendicular to that of the analyzer. An output signal from the photodetector is synchronously detected by means of a reference signal having a frequency $2f_0$. Then a synchronously detected output signal represents an amount of the antigen contained in the sample.

22 Claims, 8 Drawing Figures

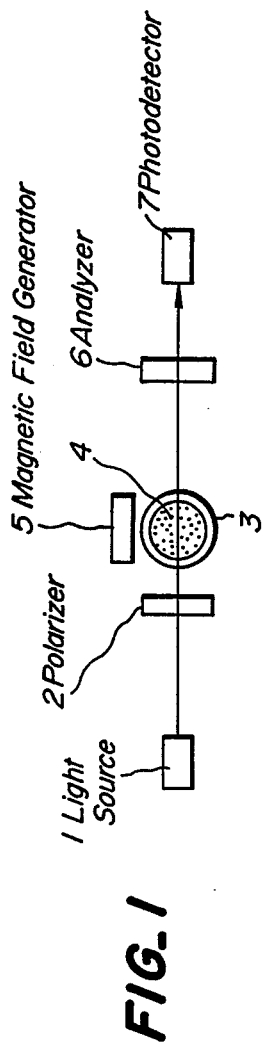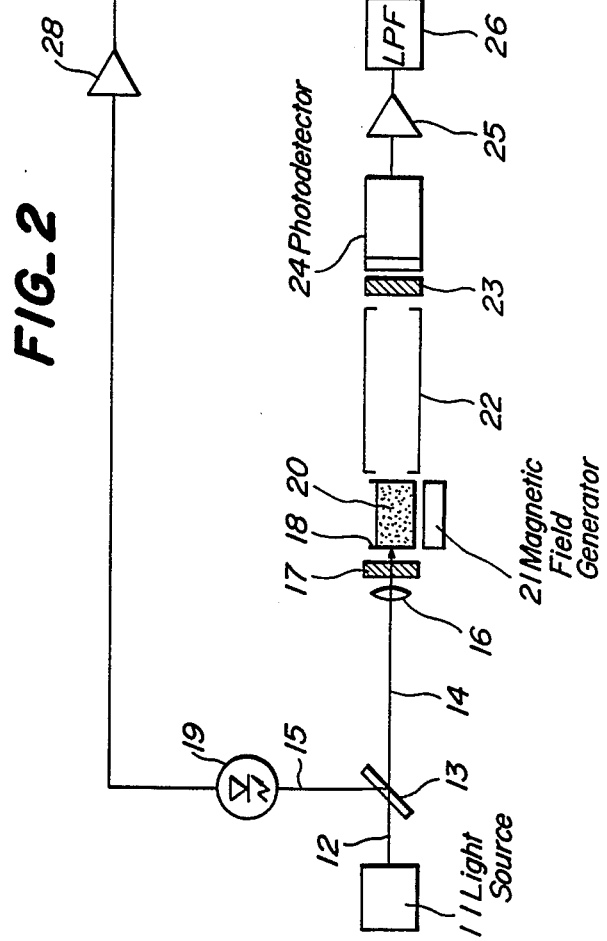

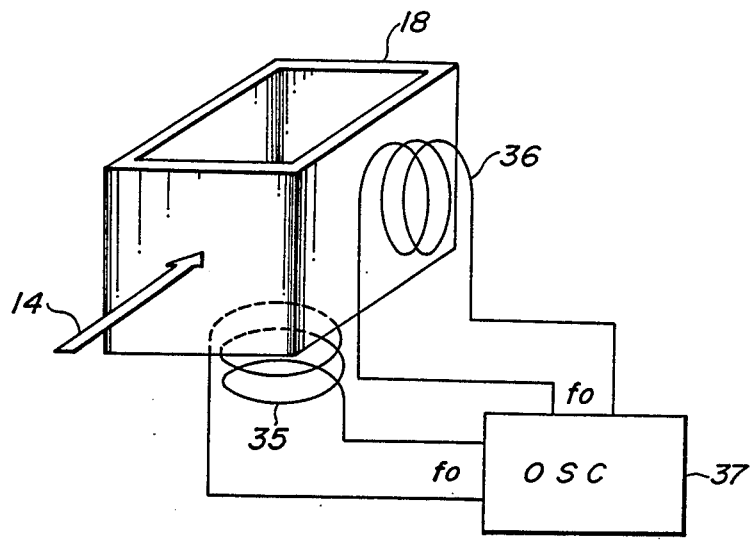
FIG_3
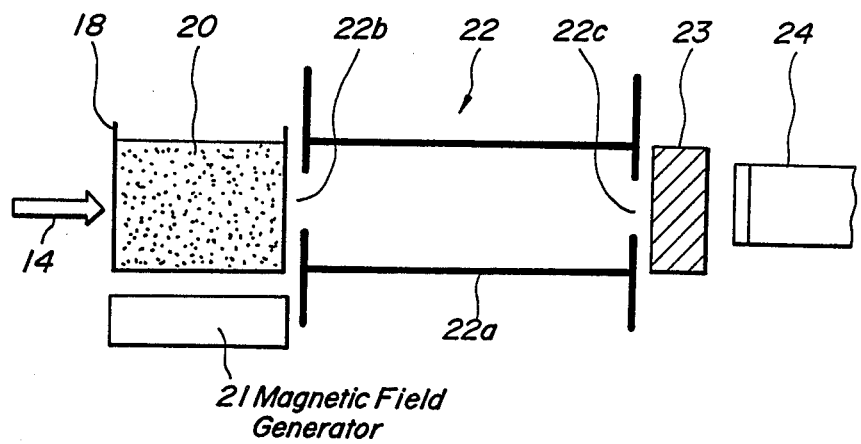
FIG_4

FIG.5
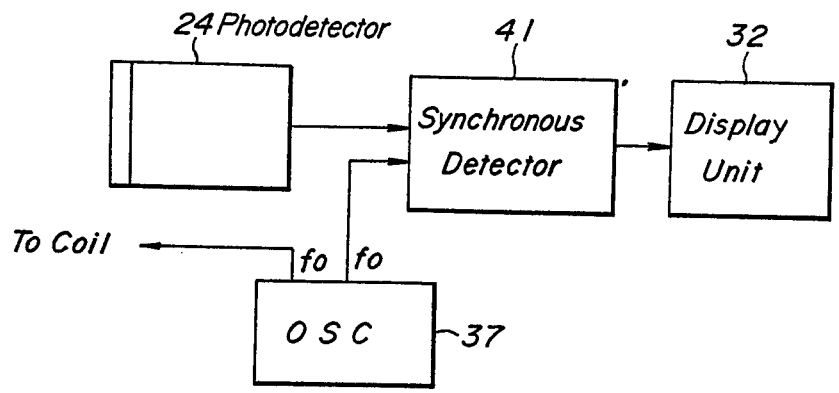
FIG.6A
FIG.6B
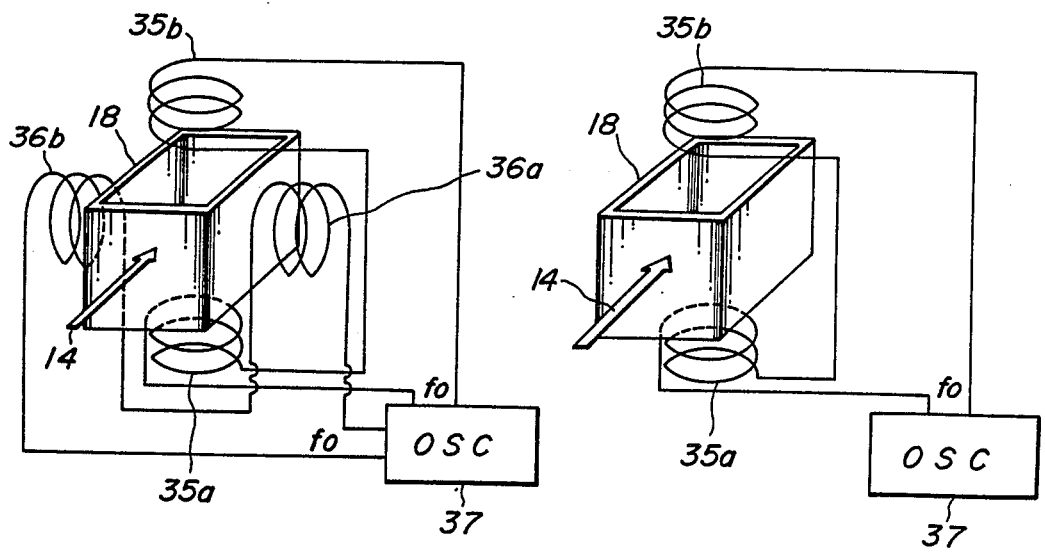

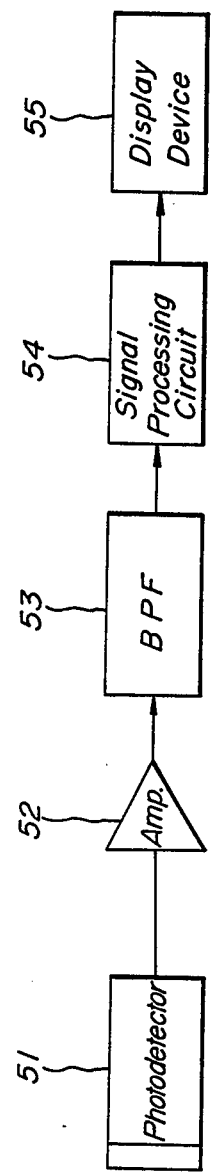

METHOD OF MEASURING SPECIFIC BINDING REACTION WITH THE AID OF POLARIZED LIGHT BEAM AND MAGNETIC FIELD

BACKGROUND OF THE INVENTION

Field of the Invention and Related Art Statements

The present invention relates to a method of measuring a specific binding reaction with the aid of a polarized light beam and a magnetic field.

There has been developed an immunological analysis for measuring immune substances, hormones, medicines, and various components such as immune regulators faintly contained in living bodies by utilizing a specific immunological reaction. It should be noted that in the present specification, the term specific binding reaction is used to express all reactions due to ligands which are reactive to specific substances. Therefore, the specific binding reaction includes not only the immunological reaction due to antigen-antibody reaction, but also the avidin-biotin reaction, protein A-IgG Fc fragment reaction and hormone-receptor reaction. For instance, the immunological analysis may be roughly classified into a labeling immunological analysis in which enzymes and isotopes are used as an indicator substance, and a non-labeling immunological analysis in which antigen-antibody complexes are directly measured.

In prior labeling immunological analysis, there have been widely known radio immuno assay (RIA), enzyme immuno assay (EIA) and fluoro immuno assay (FIA). These assays have an advantage in that a high sensitivity can be attained, but also have a drawback in that handling of isotopes and wasted liquid is difficult, measuring periods are long and labeling reagents are expensive so that the test cost, per sample, i.e. running cost is often high.

In prior non-labeling immunological analysis, there have been developed immuno electrophoresis, immuno diffusion and sedimentation. These methods have been described in detail in Japanese magazines, "Summary of Clinical Test Method" published by Kinbara and "Clinical Test", vol 22, No. 5 (1978) pp. 471–487.

In "Immuno chemistry", vol 12, No. 4 (1975) pages 349 to 351, there has been proposed one method of non-labeling immunological analysis in which an antigen or antibody bound on surfaces of fine particles is reacted with an antibody or antigen contained in a test liquid, and an average diffusion constant which is an indicia of the Brownian motion of aggregates composed of agglutinated particles is measured from a variation in a spectral width of laser light scattered from a solution of particles. This method has a merit that no reagent is used. However, since the spread of the spectrum due to the Doppler effect owing to the Brownian motion of aggregates is detected by a spectrometer, the apparatus is liable to be large in size and expensive in cost. Further, error might be induced when the spectrometer is driven mechanically, so that precision and reproducibility become worse. Moreover, in this known method in which the average diffusion constant is measured from the spectral width, the amount of available information about the antigen-antibody reaction is limited.

The present inventor has proposed, in U.S. patent application Ser. No. 754,272 filed on July 12, 1985, a method of measuring an antigen-antibody reaction, in which it is not necessary to use expensive reagents or a sepectrometer, the measurement can be carried out reproducibly at a high precision, and the measurement can be performed automatically within a relatively short time period.

This method of measuring an immunological reaction comprises the steps of:

projecting radiation into a reaction liquid containing at least antigen and antibody;

detecting radiation scattered by particulate substances in the reaction liquid;

deriving a power spectrum density of fluctuation in intensity of said scattered radiation; and measuring an antigen-antibody reaction on the basis of said power spectrum density.

After conducting various experiments and analyses, the inventor has found that if impurities such as highly polymerized substances are contained in a test liquid, the light beam is also scattered by the impurities, and thus an output signal supplied from a photodetector includes error components due to said highly polymerized substances.

SUMMARY OF THE INVENTION

The present invention has for its object to provide a novel and useful method of measuring a specific binding reaction in which the specific binding reaction can be measured very accurately without using expensive labeling reagents or an expensive and large spectrometer while the adverse influence of impurities can be avoided effectively.

According to the invention, a method of measuring a specific binding reaction comprises the steps of:

projecting polarized light to a reaction liquid containing a sample and fine particles made of magnetic material and having a ligand coated thereon, said ligand being selectively reactive with specific substances contained in the sample;

moving said particles in the reaction liquid by applying a magnetic field;

introducing light scattered by particles into an analyzer;

introducing light transmitted through said analyzer into a photodetector to produce an output signal; and processing said output signal from the photodetector to measure the specific binding reaction.

BRIEF DESCRIPTION OF THE DRAWINGS

FIG. 1 is a schematic view showing a principal construction of the specific binding reaction measuring method according to the invention;

FIG. 2 is a schematic view representing an embodiment of an apparatus for carrying out the specific binding reaction measuring method according to the invention;

FIG. 3 is a schematic view depicting an embodiment of a magnetic field generating device shown in FIG. 2;

FIG. 4 is a schematic view illustrating a construction of a collimator shown in FIG. 2;

FIG. 5 is a schematic view showing another embodiment of the specific binding reaction measuring method according to the invention;

FIGS. 6A and 6B are schematic views illustrating other embodiments of the magnetic field generating device according to the invention; and FIG. 7 is a block diagram showing another embodiment of the signal processing circuit according to the invention.

DESCRIPTION OF THE PREFERRED EMBODIMENTS

FIG. 1 is a schematic view showing a principal construction of the specific binding reaction measuring method according to the invention. Light emitted from a light source 1 is projected via a polarizer 2 to a cell 3 which contains a reaction liquid 4 consisting of a sample and fine particles made of magnetic material. The particles may have a spherical shape. Onto a surface of the particles there is fixed an antibody or antigen which is specifically reactive with an antigen or antibody contained in the sample to be analyzed. The light is polarized linearly by means of the polarizer 2 and is scattered by the particles contained in the reaction liquid 4. In this case, the polarizing condition of the scattered light is changed in accordance with the agglutinating condition of particles. Since non-agglutinated particles are spherical and have optical isotropy, they are polarized in the same direction as a vibrating direction of an electric field vector of electromagnetic waves of the linearly polarized incident light. Therefore, the light scattered by non-agglutinated particles is also linearly polarized in the same polarization plane as that of the incident light. When the antigen-antibody reaction occurs and particles are agglutinated with each other, the configuration of agglutinated particles is no longer spherical, but is deviated from the spherical shape and has an optical anisotropy. When the polarized light is scattered by the agglutinated particles having the optical anisotropy, the scattered light has different polarization components than the polarization component of the incident light.

According to the invention, both the non-agglutinated particles and agglutinated particles are moved by means of a magnetic field generated by a magnetic field generating device 5 arranged outside the cell 3. For instance, the particles may be rotated periodically in a plane perpendicular to a direction of the incident light. Since the non-agglutinated particles are spherical even if they are rotated, the polarizing direction of light scattered by the non-agglutinated particles is same as that of the incident light. However, the polarizing direction of light scattered by the agglutinated particles is rotated in accordance with the rotation of the agglutinated particles.

When the scattered light is made incident via an analyzer 6 upon a photodetector 7, an output signal of the photodetector is charged in accordance with the agglutinating condition of the particles contained in the reaction liquid 4, i.e. the antigen-antibody reaction condition. That is to say, when the polarization plane of the analyzer 6 is made identical with the polarization plane of the polarizer 2, the light scattered by the non-agglutinated particles is made incident upon the photodetector 7 together with the light scattered by the agglutinated particles. On the contrary, when the polarization plane of the analyzer 6 is made perpendicular to the polarization plane of the polarizer 2, only a part of the light scattered by the agglutinated particles is made incident upon the photodetector 7. In either case, the light scattered by the agglutinated particles and incident upon the photodetector 7 is changed at a frequency equal to twice of the rotational frequency of the particles. Therefore, it is possible to measure the immunological reaction by detecting the variation of the output signal of the photodetector 7.

FIG. 2 is a schematic view showing an embodiment of an apparatus for carrying out the immunological reaction measuring method according to the invention. In the present embodiment, use is made of a heterodyne mode in which scattered light emanating in the same direction as the incident light is detected. A light source for emitting coherent light is constructed by a He-Ne gas laser 11 emitting a laser beam having a wavelength of 632.8 nm. The light source emitting the coherent light may be formed by a solid state laser such as a semiconductor laser. A laser light flux 12 emitted from the light source 11 is divided by a half mirror 13 into light fluxes 14 and 15. The light flux 14 is collected by a condenser lens 16 and is made incident upon a cell 18 via a polarizer 17 made of a Glan-Thompson prism as linearly polarized light. The cell 18 is made of transparent quartz. The light flux 15 is made incident upon a photodetector 19 such as a silicon photodiode. Then the photodetector 19 generates a monitor signal representing a variation of the intensity of light output emitted from the light source 11.

At first, into the cell 18 is poured a buffer solution containing fine spherical particles having diameters of about 0.05–0.1 $\mu$m. The particles may be made of ferromagnetic material such as Ni, Co and alloys thereof having no or very small spontaneous magnetization. On outer surfaces of the particles are fixed an antigen or antibody such as immunoglobulin G (IgG). Next a sample containing an antibody or antigen is poured in the cell 18 to form an antigen-antibody reaction liquid 20. Beside the cell 18 there is arranged a magnetic field generating device 21. In the present embodiment, the device 21 generates a magnetic field for rotating periodically the magnetic particles in a plane perpendicular to the direction of the incident light.

Light rays scattered by the particles in the cell 18 are made incident upon a photodetector 24 via a collimator 22 having a pair of pin holes and an analyzer 23. The photodetector 24 is formed by a photomultiplier having a very high sensitivity. The analyzer 23 has a polarization plane which is different from that of the polarizer 17. In the present embodiment, the polarization plane of the analyzer 23 is perpendicular to that of the polarizer 17.

The output monitor signal from the photodetector 19 is supplied via a low noise amplifier 28 to a data processing device 27 to which is also supplied an output signal from the photodetector 24 by means of low noise amplifier 25 and low pass filter 26 having a cut-off frequency of several hundred hertz. The data processing device 27 comprises A/D converter unit 29, fast Fourier transformer (FFT) unit 30 and calculation unit 31 and processes the signals as will be explained hereinafter to derive a measurement result of the antigen-antibody reaction. The measurement result is displayed by a display device 32.

The output signal from the photodetector 24 represents an intensity of the scattered light emanating from the measuring cell 18 and is normalized by the monitor signal supplied from the photodetector 28 and averaged for a short time period. Then any fluctuation due to the variation of intensity of the laser light flux 12 emitted from the light source 11 can be removed. Next, a power spectrum density of fluctuation in intensity of scattered light is detected, and the agglutination condition of particles in the cell 18 and thus the proceeding antigen-antibody reaction is measured.

FIG. 3 is a schematic view illustrating an embodiment of the magnetic field generating device 21. The device 21 comprises a pair of coils 35 and 36 which are arranged perpendicularly to the direction of the incident light beam 14 and also are mutually perpendicular to each other. These coils 35, 36 are connected to an oscillator 37 for generating alternating currents having the same frequency $f_0$ of about 10 Hz at phases shifted by 90° from each other. The alternating currents may have sinusoidal or pulsatory shape. When the coils 35, 36 generate alternating magnetic fields having a phase difference of 90° and perpendicular to each other, there is produced in the cell 18 a rotating magnetic field. When the magnetic particles are subjected to such a rotating magnetic field, they are rotated at the frequency $f_0$ in a plane perpendicular to the direction of the incident light beam 14.

As explained above, when the particles are subjected to the alternating magnetic fields having the phase difference of 90° and perpendicular to each other in the plane perpendicular to the direction of the incident light, the magnetic particles are rotated at the same frequency as that of the alternating magnetic field due to the magnetic induction.

FIG. 4 is a schematic view illustrating a detailed construction of the collimator 22 shown in FIG. 2. The collimator 22 comprises a tube 22a which is made of opaque material so as to remove the influence of external light. Further, an inner wall of the tube 22a is provided with an anti-reflecting coating. On both ends of the tube 22a there are provided pin holes 22b and 22c. The collimator 22 is used to limit the field of view of the photodetector 24 so as to decrease the influence of stray light. The pin holes 22b, 22c have a diameter of 0.3 mm and are separated from each other by 30 cm.

When the antigen-antibody reaction does not occur in the cell 18 and the particles are not agglutinated together, the spherical particles still have optical isotropy, and thus even if the particles are rotated, the scattered light has the same polarizing direction as that of the incident linearly polarized light 14. Therefore, the scattered light is not transmitted through the analyzer 23 and the output signal of the photodetector 24 theoretically becomes zero. Contrary to this, when the antigen-antibody reaction occurs and the particles are agglutinated with each other, agglutinated particles show the optical anisotropy, and thus the scattered light has polarized components perpendicular to the polarization plane of incident light. Then a part of the scattered light is transmitted through the analyzer 23 and the photodetector 24 produces a non-zero output signal. Moreover, the polarizing direction of the scattered light due to the agglutinated particles is rotated in accordance with the rotation of the particles due to the magnetic field. Therefore, the scattered light received by the photodetector 24 includes a component which varies at a frequency $2f_0$ equal to twice the frequency $f_0$ of the alternating magnetic field. If impurities such as highly polymerized substances are contained in the test sample such as a serum sample, light scattered by these impurities may also include a polarization component perpendicular to the polarization plane of the linearly polarized incident light, and thus a part of the light scattered by the impurities might be transmitted through the analyzer 23. Therefore, the output signal from the photodetector 24 might include a noise component superimposed upon the signal due to the agglutinated particles. However, since these impurities are not magnetic, they are not rotated by the magnetic field and the output signal component due to the impurities is not changed in synchronism with the alternating magnetic field. Therefore, by detecting the output signal from the photodetector 24 on the basis of the frequency $2f_0$, it is possible to select only the signal component due to the agglutinated particles. In this manner, according to the invention the antigen-antibody reaction can be detected at a high S/N ratio and with high sensitivity.

In the present embodiment, the power spectrum density of fluctuation in intensity of the scattered light is detected. To this end, the output signal from the photodetector 24 is supplied to the data processing device 27 via the amplifier 25 and low pass filter 26 and is processed therein together with the output monitor signal from the photodetector 19 to derive the power spectrum density of fluctuation in intensity of the scattered light. A power spectrum density S(f) of the stationary stochastic process x(t) may be expressed as follows:

$$S(f) = \lim_{T \to \infty} \frac{1}{2T} < \left| \int_{-T}^{T} x(t) e^{-2\pi i f t} dt \right|^2 >$$

On the basis of this equation, the Fourier transformation is performed to calculate the power spectrum density. The output signal from the photodetector 24 is amplified by the low noise amplifier 25 in such a manner that signal values can cover a wide range of A/D conversion quantum levels, and data thus quantized is calculated by a microprocessor to derive the power spectrum density. From the power spectrum density, the condition of the immunological reaction is measured and is displayed numerically on the display unit 32.

As explained above, when the agglutinated particles are rotated at the frequency $f_0$, the optical anisotropy of the agglutinated particles is changed periodically at the frequency $2f_0$. Therefore, by detecting an amount of a component of the power spectrum density at the frequency $2f_0$ or a configuration of the power spectrum density near the frequency $2f_0$, it is possible to identify the antigen in the sample or to measure an amount of the antigen contained in the sample.

In the present embodiment, since it is not necessary to use expensive and cumbersome labeling reagents such as enzymes and radioisotopes, the measurement can be performed in an easy and less expensive manner. Further, the accuracy and reproducibility of the measurement according to the invention are much higher than those of the non-labeling immuno-analyses such as immuno-electrophoresis, immuno-diffusion and sedimentation, and thus it is possible to obtain reliable measurement results. Moreover, as compared with the known method in which the average diffusion constant is derived from the variation of the spectrum width of the scattered light, in the method according to the invention it is no longer necessary to use the expensive and large spectrometer. Therefore, the whole apparatus can be made less expensive in cost, small in size and light in weight. Moreover, since the measurement is based on the power spectrum density of fluctuation in intensity of the scattered light, it is possible to obtain a larger amount of information about the antigen-antibody reaction.

FIG. 5 is a schematic view illustrating a major part of another embodiment of the immunological reaction measuring apparatus according to the invention. In the present embodiment, the output signal from the photodetector 24 is supplied to a synchronous detector unit 41 to which is also supplied a reference signal of the frequency $f_0$ from the oscillator unit 37, and a signal component having the frequency $2f_0$ is synchronously detected. An output signal thus detected is displayed on the display unit 32.

In this embodiment, the output signal from the synchronous detector unit 41 is dependent solely upon the agglutinating condition, i.e. the concentration of the antigen contained in the sample. Therefore, when a calibration curve is preliminarily derived by using standard samples having known antigen concentrations, it is possible to detect precisely unknown concentrations of the antigen contained in samples. As compared with the previous embodiment, in the present embodiment the signal processing is much simpler and the measuring time period can be shortened. Further, the measurement can be carried out at a higher S/N ratio and with a higher accuracy.

The present invention is not limited to the embodiments explained above, but many alternations and modifications can be effected within the scope of the invention. In the above embodiment use is made of immunoglobulin G (IgG), but any substance such as immunoglobulin A(IgA), IgM, IgD, IgE, Australia antigen, syphilis antigen and insulin which produce agglutination by the antigen-antibody reaction may be used. Further, other specific binding reactions than the immunological antigen-antibody reaction may be also measured. For instance, by using particles having hormones coated thereon, it is possible to analyze receptors contained in samples. Further, when use is made of particles having avidin, biotin, protein A or IgG Fc fragment coated thereon, biotin, avidin, IgG Fc fragment or protein A contained in samples may be measured. In the above embodiment, an antibody is fixed on the surfaces of particles to detect an antigen contained in a sample, but an antibody contained in a sample may be detected by using particles having an antigen coated thereon. Moreover, in the above embodiment, the antigen-antibody reaction liquid is contained in the cell and the measurement is effected in the batch mode, but according to the present embodiment the measurement may be performed in the flow mode in which the antigen-antibody reaction liquid continuously flows through a flow cell. In the above embodiment, use is made of the laser light source emitting coherent light, but use may be made of light sources generating incoherent light. Further, the magnetic particles are not always spherical, but may be nonspherical as long as a particle size is smaller than several tenths of a micron.

In the above embodiment, the polarization plane of the analyzer 23 is perpendicular to that of the polarizer 17, and thus light scattered by non-agglutinated particles is not made incident upon the photodetector 24. Therefore, the immunological reaction may be detected accurately from an intensity or an average value of the output signal of the photodetector 24. Moreover, the polarization plane of the analyzer 23 may be set arbitrarily with respect to the polarization plane of the polarizer 17.

In the embodiment shown in FIG. 3, the two coils 35 and 36 are arranged perpendicularly to the direction of the incident light and are mutually perpendicular to each other. In an embodiment illustrated in FIG. 6A, a pair of coils 35a and 35b are arranged in opposite to each other with respect to the cell 18 and a pair of coils 36a and 36b are arranged in opposite to each other with respect to the cell 18. It should be noted that it is not always necessary to rotate the particles in a plane perpendicular to the direction of the incident light. Further, by arranging a pair of coils 35a and 35b in opposite to each other with respect to the cell 18 and connecting these coils in series to the oscillator unit 37 as shown in FIG. 6B, it is possible to swing reciprocally at the frequency $f_0$. Also in this case, the output signal from the photodetector is changed periodically at the frequency $2f_0$. Further, the particle may be moved by intermittently supplying a direct current to the coils, or by rotating a permanent magnet without using the coils. It should be further noted that prior to the measurement, the reaction liquid 20 may be subjected intermittently to a uniform or non-uniform magnetic field by means of the magnetic field generating device 21 to temporarily orient the particles in the direction of the magnetic field. Then the particles are stirred and the antigen-antibody reaction is promoted. In this manner, the measuring time period can be shortened materially.

In the above embodiment, the light flux scattered in the same direction as that of the incident light is detected, but a light flux scattered laterally may be detected to measure the antigen-antibody reaction.

In the embodiment explained above, the linearly polarized light beam is made incident upon the cell 18, but it is also possible to use circularly polarized or elliptically polarized light beam. In such a case, a light flux scattered by particles may be incident upon the analyzer 17 by means of a quarter wavelength plate.

In the present embodiment, since magnetic particles are moved, rotated or swung by means of the magnetic field, it is possible to detect magnetic particles in a field of environmental hygiene such as detection of atmospheric pollution or detection of water quality.

In the embodiment shown in FIG. 5, the signal component having the given frequency $2f_0$ is derived by the synchronous detector. According to the invention, it is also possible to derive the desired signal component with the aid of a band pass filter. FIG. 7 is a block diagram illustrating such an embodiment. In this embodiment, an output signal from a photodetector 51 receiving light scattered by particles and then transmitted through an analyzer is amplified by a low noise amplifier 52. Then an amplified signal from the amplifier 53 is passed through a band pass filter 53 having a center frequency $2f_0$ equal to twice of a frequency $f_0$ at which the magnetic particles are rotated in the test liquid. Then, an output signal from the band pass filter 53 is consisting of a signal component having the frequency $2f_0$. This signal is further supplied to a signal processing circuit 54 to measure a degree of the agglutination of magnetic particles, i.e. the agglutination reaction, and a measured result is displayed by a display device 55. It should be noted that the construction of the signal processor of the present embodiment is much simpler than the previous embodiments.

As explained above in detail, according to the invention the magnetic particles are moved by the varying magnetic field and a component of the scattered light varying in accordance with the movement of the particles is selectively derived. Therefore, the influence of impurities such as highly polymerized substances contained in the test liquid can be removed to a great extent. Therefore, the highly accurate and sensitive measurement can be performed within a very short time period. According to the invention, it is possible to use magnetic particles other than those wholly made of magnetic material. For instance, it is possible to use magnetotactic bacteria particles such as aquaspirillum nagnetotacticum and magnetotactic coccus, these particles containing very fine magnetic particles called magnetosome. The magnetosome is made of $Fe_3O_4$ particles having an average diameter of 0.05 to 0.15 $\mu$m. Further it is also possible to use a magnetic microcapsule having very fine magnetic particles surrounded or wrapped by a polymer film.

What is claimed is:

1. A method of measuring a specific binding reaction comprising the steps of:
   projecting polarized light to a reaction liquid containing a sample and fine particles made of magnetic material and having a ligand coated thereon, said ligand being selectively reactive with a specific substance contained in the sample;
   moving said particles in the reaction liquid by applying a magnetic field;
   introducing light scattered by said particles into an analyzer;
   introducing light transmitted through said analyzer into a photodetector to produce an output signal; and
   processing said output signal from the photodetector to measure the specific binding reaction.

2. A method according to claim 1, wherein said fine particles have coated thereon a ligand selected from a group consisting essentially of an antigen, antibody, avidin, biotin, protein A, IgG Fc fragment and hormone.

3. A method according to claim 1, wherein light emitted from a light source is made incident upon the reaction liquid by means of a polarizer.

4. A method according to claim 3, wherein said analyzer has a polarization plane different from a polarization plane of the polarizer.

5. A method according to claim 1, wherein said magnetic field is so applied that the particles are moved periodically at a given frequency $f_0$.

6. A method according to claim 5, wherein light scattered by the particles in the same direction as that of the incident light is made incident upon the analyzer, and the particles are moved in a plane perpendicular to said direction.

7. A method according to claim 5, wherein said polarization plane of the analyzer is perpendicular to the polarization plane of the polarizer.

8. A method according to claim 1, wherein said magnetic particles are spherical.

9. A method according to claim 5, wherein said output signal of the photodetector is supplied to a band pass filter having a center frequency $2f_0$ equal to twice said given frequency to derive a signal component having the frequency $2f_0$.

10. A method according to claim 5, wherein said particles are rotated at said frequency $f_0$.

11. A method according to claim 10, wherein said varying magnetic field for rotating the particles is generated by a pair of coils arranged perpendicularly to each other, said pair of coils being energized with alternating currents having the same frequency $f_0$, but having a phase difference of 90°.

12. A method according to claim 10, wherein said varying magnetic field is generated by a first pair of coils arranged in opposite to each other with respect to the reaction liquid and a second pair of coils also arranged in opposite to each other with respect to the reaction liquid, said first and second pairs of coils being perpendicular to each other and being energized with alternating currents having the same frequency $f_0$, but having a phase difference of 90°.

13. A method according to claim 5, wherein said particles are swung at said frequency $f_0$.

14. A method according to claim 13, wherein said magnetic field for swinging the particles is generated by a pair of coils arranged opposite to each other with respect to the reaction liquid, said pair of coils being energized with an alternating current having the frequency $f_0$.

15. A method according to claim 5, wherein said output signal of the photodetector is supplied to a fast Fourier transformer to derive a power spectrum density of fluctuation in intensity of the scattered light and at least a component having a frequency $2f_0$ equal to twice of said given frequency $f_0$ is selected from the power spectrum density.

16. A method according to claim 15, wherein the immunological reaction is measured by detecting an amount of the component having the frequency $2f_0$.

17. A method according to claim 15, wherein the immunological reaction is measured by detecting a shape of a part of the power spectrum density including the component having the frequency $2f_0$.

18. A method according to claim 5, wherein said output signal of the photodetector is detected in synchronism with the varying magnetic field.

19. A method according to claim 18, wherein said output signal of the photodetector is supplied to a synchronous detector to which is also supplied a reference signal having a frequency $2f_0$ equal to twice of said given frequency $f_0$, and the immunological reaction is measured in accordance with an amplitude of an output signal of the synchronous detector.

20. A method according to claim 1, wherein said magnetic particles are made of ferromagnetic material.

21. A method according to claim 20, wherein said magnetic particles are made of Ni, Co or alloys thereof.

22. A method according claim 21, wherein said magnetic particles have diameters of 0.05–0.1 $\mu$m.

* * * * *

UNITED STATES PATENT AND TRADEMARK OFFICE
CERTIFICATE OF CORRECTION

PATENT NO. : 4,725,140
DATED : February 16, 1988
INVENTOR(S) : Toshimitsu Musha

It is certified that error appears in the above-identified patent and that said Letters Patent is hereby corrected as shown below: Title page:

In the Foreign Application Priority Data change "60-256545" to --60-257545--.

Signed and Sealed this

Twenty-ninth Day of November, 1988

Attest:

DONALD J. QUIGG

Attesting Officer

Commissioner of Patents and Trademarks